(12) United States Patent
Babkin et al.

(10) Patent No.: US 10,952,676 B2
(45) Date of Patent: Mar. 23, 2021

(54) ENDOESOPHAGEAL BALLOON CATHETER, SYSTEM, AND RELATED METHOD

(71) Applicant: ADAGIO MEDICAL, Inc., Laguna Hills, CA (US)

(72) Inventors: Alexei V. Babkin, Dana Point, CA (US); Peter Littrup, Bloomfield Hills, MI (US); Steven W. Kovalcheck, San Diego, CA (US)

(73) Assignee: Adagio Medical, Inc., Laguna Hills, CA (US)

( * ) Notice: Subject to any disclaimer, the term of this patent is extended or adjusted under 35 U.S.C. 154(b) by 799 days.

(21) Appl. No.: 15/028,927

(22) PCT Filed: Oct. 12, 2014

(86) PCT No.: PCT/US2014/060207
§ 371 (c)(1),
(2) Date: Apr. 12, 2016

(87) PCT Pub. No.: WO2015/057533
PCT Pub. Date: Apr. 23, 2015

(65) Prior Publication Data
US 2016/0249859 A1    Sep. 1, 2016

Related U.S. Application Data

(60) Provisional application No. 61/890,835, filed on Oct. 14, 2013.

(51) Int. Cl.
*A61B 5/00* (2006.01)
*A61B 8/12* (2006.01)
(Continued)

(52) U.S. Cl.
CPC .......... *A61B 5/6853* (2013.01); *A61B 1/2736* (2013.01); *A61B 5/044* (2013.01);
(Continued)

(58) Field of Classification Search
CPC combination set(s) only.
See application file for complete search history.

(56) References Cited

U.S. PATENT DOCUMENTS 4,085,757 A * 4/1978 Pevsner ........... A61B 17/12031
604/907
4,543,960 A  10/1985 Harui
(Continued)

FOREIGN PATENT DOCUMENTS

JP  2008-515469    5/2008
WO  2004/064914    8/2004
(Continued)

OTHER PUBLICATIONS

Office Action dated Jul. 26, 2018 for U.S. Appl. No. 14/915,631.
(Continued)

*Primary Examiner* — Pascal M Bui Pho
*Assistant Examiner* — Yi-Shan Yang
(74) *Attorney, Agent, or Firm* — Richard Batt

(57) ABSTRACT

An endoesophageal balloon and catheter for operation with a transesophageal echocardiography (TEE) probe includes an inflatable balloon body disposed over the ultrasound element of the TEE probe, a liquid inflow lumen in fluid communication with the balloon, and a liquid outflow lumen in fluid communication with the balloon. The balloon is inflated with an acoustically transmitting liquid.

10 Claims, 9 Drawing Sheets

(51) Int. Cl.
    *A61B 8/00*           (2006.01)
    *A61B 1/273*         (2006.01)
    *A61B 5/044*         (2006.01)
    *A61B 18/02*         (2006.01)
    *A61B 18/00*         (2006.01)
    *A61B 8/08*           (2006.01)
    *A61B 90/00*         (2016.01)
    *A61B 17/00*         (2006.01)

(52) U.S. Cl.
    CPC .............. *A61B 8/12* (2013.01); *A61B 8/4281* (2013.01); *A61B 8/445* (2013.01); *A61B 18/02* (2013.01); *A61B 8/0841* (2013.01); *A61B 8/0883* (2013.01); *A61B 8/4488* (2013.01); *A61B 17/00234* (2013.01); *A61B 2017/00278* (2013.01); *A61B 2018/0022* (2013.01); *A61B 2018/00041* (2013.01); *A61B 2018/00351* (2013.01); *A61B 2018/00357* (2013.01); *A61B 2018/00577* (2013.01); *A61B 2018/0212* (2013.01); *A61B 2090/3784* (2016.02)

(56) References Cited

U.S. PATENT DOCUMENTS

| | | | |
|---|---|---|---|
| 4,834,102 A | | 5/1989 | Schwarzchild |
| 4,841,977 A | | 6/1989 | Griffith |
| 5,267,221 A | | 11/1993 | Miller |
| 5,421,338 A | * | 6/1995 | Crowley ................ A61B 5/416 600/463 |
| 5,499,630 A | * | 3/1996 | Hiki ...................... A61B 1/0051 600/104 |
| 6,139,502 A | | 10/2000 | Fredriksen |
| 6,270,489 B1 | * | 8/2001 | Wise .................... A61M 25/003 604/508 |
| 6,936,045 B2 | | 8/2005 | Yu |
| 7,083,612 B2 | | 8/2006 | Littrup |
| 7,160,290 B2 | | 1/2007 | Eberl |
| 7,195,625 B2 | | 7/2007 | Lentz |
| 7,273,479 B2 | | 9/2007 | Littrup |
| 7,410,484 B2 | | 8/2008 | Littrup |
| 8,012,147 B2 | | 9/2011 | Lafontaine |
| 8,118,743 B2 | | 2/2012 | Park |
| 8,387,402 B2 | | 3/2013 | Littrup |
| 8,740,891 B2 | | 6/2014 | Babkin |
| 8,740,892 B2 | | 6/2014 | Babkin |
| 8,926,649 B2 | * | 1/2015 | Krolik .............. A61B 17/22032 606/194 |
| 2006/0058598 A1 | * | 3/2006 | Esposito ............ A61B 18/1492 600/374 |
| 2008/0281143 A1 | * | 11/2008 | Lubock ................. A61N 5/1015 600/3 |
| 2010/0057063 A1 | | 3/2010 | Arless |
| 2010/0152590 A1 | * | 6/2010 | Moore ............... A61B 1/00082 600/466 |
| 2010/0179424 A1 | * | 7/2010 | Warnking ............. A61N 7/022 600/437 |
| 2011/0071395 A1 | | 3/2011 | Miller |
| 2011/0162390 A1 | | 7/2011 | Littrup |
| 2011/0184399 A1 | | 7/2011 | Wittenberger |
| 2012/0022338 A1 | * | 1/2012 | Subramaniam ...... A61B 5/0066 600/301 |
| 2012/0059364 A1 | | 3/2012 | Baust |
| 2012/0253336 A1 | | 10/2012 | Littrup |
| 2013/0073014 A1 | | 3/2013 | Lim |
| 2013/0165823 A1 | * | 6/2013 | Ishibashi ............ A61B 1/00082 601/2 |
| 2014/0276079 A1 | * | 9/2014 | Yamagata .............. A61B 8/445 600/459 |
| 2015/0141917 A1 | * | 5/2015 | Tilson ................... A61F 2/2433 604/103.07 |

FOREIGN PATENT DOCUMENTS

| | | | | |
|---|---|---|---|---|
| WO | WO 2006122348 A1 | * | 11/2006 | .............. A61B 8/06 |
| WO | 2009/009398 | | 1/2009 | |
| WO | WO 2013/013098 | | 1/2013 | |
| WO | WO 2013/013099 | | 1/2013 | |
| WO | WO 2015/160574 | | 10/2015 | |

OTHER PUBLICATIONS

Office Action dated Jul. 13, 2018 for U.S. Appl. No. 15/028,925.
Supplemental European Search Report dated Apr. 23, 2018 for EP15858716.
Australian Examination Report No. 1, dated Jul. 31, 2018 for 2014327045.
International Search Report dated Mar. 18, 2015 for PCT/US14/56839.
International Search Report dated Jan. 21, 2015 for PCT/US2014/059684.
International Search Report dated Mar. 17, 2015 for PCT/US2014/060207.

* cited by examiner

ENDOESOPHAGEAL BALLOON CATHETER, SYSTEM, AND RELATED METHOD

CROSS-REFERENCE TO RELATED APPLICATIONS

The present application claims the benefit of priority to U.S. Provisional Application No. 61/890,835, filed Oct. 14, 2013, the entire disclosure of which is incorporated herein by reference in its entirety.

BACKGROUND

This disclosure is generally directed to endocavitary imaging systems, and more particularly, to transesophageal echocardiography (TEE). One embodiment is directed to devices and methods to optimize TEE visualization of left atrial wall ablation for treatment of atrial fibrillation.

Various non-invasive, semi-invasive and invasive ultrasound imaging systems have been described to view tissue structures within a human body, such as the heart structures, the abdominal organs, the fetus, and the vascular system. A challenge for any ultrasound image system is to have a sufficient contact of the transducer head to the target tissue being scanned, as well as an ultrasound transmissible, or coupling, agent to avoid the disruption by intervening air. Air contact with the transducer surface represents a markedly lower sound speed than adjacent tissue, resulting in massive ultrasound reflection at the tissue interface with minimal penetration of ultrasound signals and therefore minimal signals returning from the tissue to the transducer to make an image. The most common coupling agent is accomplished by ultrasound gel. Therefore, imaging a body part usually requires direct contact with tissue and thereby limits accurate visualization of tissues within the near-field of the transducer.

Another challenge in ultrasound image systems is placing targets within the higher resolution focal zone of a transducer. Still another challenge is to increase the field of view in the near field including increasing the filed of view over longer segments for both curved and linear arrays.

Various patents have addressed some of the above shortcomings including U.S. Pat. No. 4,543,960 to Harui et al.; U.S. Pat. No. 4,841,977 to Griffith et al.; U.S. Pat. No. 8,118,743 to Park et al.; and U.S. Pat. No. 6,139,502 to Fredriksen. In the '502 Patent to Fredriksen, for example, a standoff from the tissues is described to improve the field of view.

Transesophageal echocardiography (TEE) also suffers from the above described challenges. Nearly all current TEE transducers produce a sector image which markedly limits the field of view (FOV), particularly in the near field. The near field is thus viewed as a point source with the imaging sector expanding from that point on the esophageal wall. Much of the operator-dependent "art" of TEE scanning thus requires a physician imager to be able to manipulate the articulated flexible tip of the transducer head into a position that maintains imaging contact, yet still places the anatomic target to be imaged within the sector FOV. Anatomically, this places severe limitations on imaging any extent of the left atrial wall since it generally immediately abuts the esophageal wall in the near field. Very little extent of the left atrial wall can thus be seen within the near field apex of the usual sector image, making visualization or monitoring of any procedure addressing the left atrial wall. Suboptimal, if not impractical.

TEE scanning during left atrial wall ablation for treatment of atrial fibrillation has additional challenges related to safety. TEE is generally considered a well-tolerated procedure that has minimal side effects related to the actual scanning of the heart and is considered safe for the esophageal wall. However, severe pressure or manipulation of the transducer head has been known to cause rare pressure damage or small tears in the esophageal lining. Moreover, even the minor pressure asserted to again good imaging contact further presses into the adjacent left atrial wall, such that minimal FOV and extent of the left atrial wall is presented to the imager. The numerous ablation foci required to terminate atrial fibrillation are thus poorly seen, especially when they need to extend to most, if not all, of the associated entrances of the pulmonary veins where the foci of abnormal electrical activity causing atrial fibrillation frequently arise. The minor scanning pressure of the TEE transducer head also limits the thin space of safety between the left atrial wall and the adjacent esophageal wall. Penetration into the esophageal wall of any ablation of the left atrial wall thus presents a potential life-threatening communication between the beating heart and the esophageal lumen. Patients have died from exsanguination when a left atrial wall ablation site breaks down and allows communication of the left atrium with the esophageal lumen. Therefore, nearly all monitoring of the ablation is required to stop left atrial fibrillation are generally performed by fluoroscopic imaging and/or sophisticated electrical sensing processes that target the origin of the fibrillation.

Improvements in TEE imaging the left atrial wall during ablation are thus needed to make visualization even practical, let alone safe.

There are several medical procedures where ultrasound imaging systems are not yet widely used. Currently, for example, interventional cardiologists use mainly fluoroscopic imaging for guidance and placement of devices in the vasculature or in the heart. These procedures are usually performed in a cardiac catheterization laboratory (Cathlab) or an electrophysiology laboratory (EPlab). During cardiac catheterization, a fluoroscope uses X-rays on a real-time frame rate to give the physician a transmission view of a chest region, where the heart resides. A bi-plane fluoroscope, which has two transmitter-receiver pairs, mounted at 90° to each other, provides real-time transmission images of the cardiac anatomy. These images assist the physician in positioning various catheters by providing him (or her) with a sense of the three-dimensional geometry of the heart.

While fluoroscopy is a useful technique, it does not provide high quality images with good contrast in soft tissues. Furthermore, the physician and the assisting medical staff need to cover themselves with a lead suit and need to reduce the fluoroscopic imaging time whenever possible to lower their exposure to X-rays. In addition, fluoroscopy may not be available for some patients, for example, pregnant women, due to the harmful effects of the X-rays. Recently, transthoracic and transesophageal ultrasound imaging have been very useful in the clinical and surgical environments, but have not been widely used in the Cathlab or EPlab for patients undergoing interventional techniques.

Therefore there is a need for transesophageal ultrasound systems, apparatuses and methods that can provide atraumatic, fast and computationally inexpensive real-time imaging. The images should enable accurate, large-field of view, and increased near field visualization of the internal anatomy that includes various structures and provide selected views of the tissue of interest.

There is a need for transesophageal ultrasound imaging systems, apparatuses and methods that can provide tissue contact with the esophageal wall over a greater extent, thereby allowing an improved imaging standoff to place the left atrial wall within the improved focal zone of the transducer, as well as providing the associated greater FOV of the entire heart.

There is a need for transesophageal ultrasound imaging systems, apparatuses and methods that can provide a mechanism by which the temperature of the esophageal wall can be regulated to prevent either hot or cold lethal temperatures from the left atrial wall extending into the esophageal lumen.

SUMMARY

Embodiments of the present invention assist echocardiographic imaging probes such as a transesophageal echocardiography (TEE) probe. Such TEE probes generally comprise a TEE probe shaft, a TEE probe head, and a probe window through which ultrasound is sent and received to visualize a target region in a patient.

In embodiments an endoesophageal balloon (EEB) catheter comprises a flexible elongate sheath, an expandable member such as a balloon, and an optional elongate stiffener member to direct the balloon expansion towards the target tissue to be imaged. The EEB catheter is advanced through the mouth, and into the esophagus. The balloon is filled with a liquid such as water. The TEE probe is advanced into the sheath, and activated to image the target region through the liquid medium contained within the balloon. The inflated balloon serves to increase the stand off distance from the target tissue, thereby increasing the field of view.

In embodiments an endoesophageal balloon comprises an inflatable or elastic body, and an internal chamber. The internal chamber is sized to fit around the TEE probe head. The balloon has a proximal region or neck portion to snugly fit around a distal section of the TEE probe shaft. A liquid inflow tube is in fluid connection with the internal chamber and extends proximally from the inflatable balloon. A liquid outflow tube is in fluid connection with the internal chamber and extends proximally from the inflatable balloon.

In embodiments a connector holds and creates a liquid tight seal between the inflatable balloon and the TEE probe shaft. In embodiments, the connector is movably engaged with a lip or indent on the proximal region of the balloon. The connector can be ring-shaped shaped such as but not limited to an o-ring.

In embodiments the body of the balloon comprises a varying wall thickness such that the portion of the balloon covering the probe window is displaced from the probe window when a liquid is delivered into the internal chamber. A portion of the balloon on the backside of the probe head is restricted, and not displaced, when the liquid is delivered into the internal chamber. The displacement caused by the preferential expansion of the balloon creates a stand off from the target tissue.

In embodiments the endoesophageal balloon is adapted to be detached from the TEE probe.

In embodiments an endoesophageal balloon catheter system comprises an ultrasonic imaging probe having a probe shaft, a probe head for imaging a target organ, and an endoesophageal balloon as described herein. In embodiments the endoesophageal balloon catheter system may further comprise a pump or fluid transport means to circulate liquid to and from the internal chamber via the inflow and outflow tubes respectively.

In embodiments an endoesophageal balloon catheter comprises an endoesophageal balloon (EEB) as in any one of the embodiments described herein, an elongate catheter shaft comprising a liquid inflow channel, a liquid outflow channel, and a probe channel for slidably receiving the TEE probe shaft and TEE probe head. The EEB balloon is inflatable and deflatable upon delivery and withdrawal of liquid through the inflow channel and outflow channel respectively. A sealing member in the vicinity of the distal region of the elongate shaft accepts the TEE probe head there through, and forms a liquid tight seal with the TEE probe shaft and the balloon, thereby prohibiting liquid from passing there through when the TEE probe head is disposed within the balloon, and the balloon is inflated with the liquid.

In embodiments the sealing member is a gasket, valve, o-ring or an inflatable O-ring incorporated into the balloon wall to allow more circumferential pressure around the TEE shaft to minimize fluid leakage.

In embodiments a catheter shaft comprises a body defining the probe channel such that the probe channel is open, and snaps onto the TEE probe shaft.

In embodiments an endoesophageal balloon catheter system comprises an ultrasonic imaging probe insertable through an elongate probe channel of an EEB catheter as described herein. The endoesophageal balloon catheter system may further comprise a pump to circulate liquid to and from the balloon via the inflow and outflow channels respectively.

In embodiments the endoesophageal device comprises a reinforcing member causing the balloon to preferentially expand away from the TEE probe window when the TEE probe head is disposed within the internal chamber and the a liquid is delivered therein. The reinforcing member may be an elongate stiffener such as a wire, tube, or ribbon.

In embodiments the reinforcing member is a clamp affixed to the TEE probe head. The clamp can have a wide variety of shapes including, for example, a c-shaped cross section, along with covering the distal tip of the transducer to prevent expansion of the balloon away from the imaging a window and into the distal esophagus, respectively.

In embodiments a method for visualizing an endo-cardio procedure in the heart comprises inserting a head of a TEE probe within an inflatable balloon; advancing the head of the TEE probe into the esophagus; inflating the balloon with a liquid; and transmitting ultrasonic energy from an ultrasonic array present in the head of the TEE probe, through the liquid, through a wall of the balloon, and into a target region to be visualized.

In embodiments, the interior of the balloon may be evacuated and or wetted prior to inserting the head of the TEE probe in the balloon. The TEE probe head may be inserted into the balloon. Then, the balloon may be deflated. The assembly may then be advanced into the tissue lumen.

In embodiments a method for visualizing an endo-cardio cryoablation procedure in the heart comprises inserting a balloon catheter assembly into the esophagus; inserting an ultrasound probe into the esophagus, inflating the balloon with a liquid; and transmitting ultrasonic energy from the ultrasonic sensor, through the balloon, and into a target region. The step of inserting the probe into the esophagus is performed by inserting the probe within a probe channel of the balloon catheter. The step of inserting the probe into the esophagus is performed by inserting the probe along the side the catheter. The method can further comprise circulating the liquid to and from the balloon. The method may further comprise visualizing a chamber of the heart.

In embodiments a method for supporting echography of an ablation procedure in a patient, and for mitigating thermal damage to collateral tissue of the patient comprises circulating an acoustically conductive liquid through an inflatable balloon surrounding an imaging probe head during the ablation procedure, thereby maintaining a collateral tissue temperature within a predetermined range.

DETAILED DESCRIPTION

Figure 1:
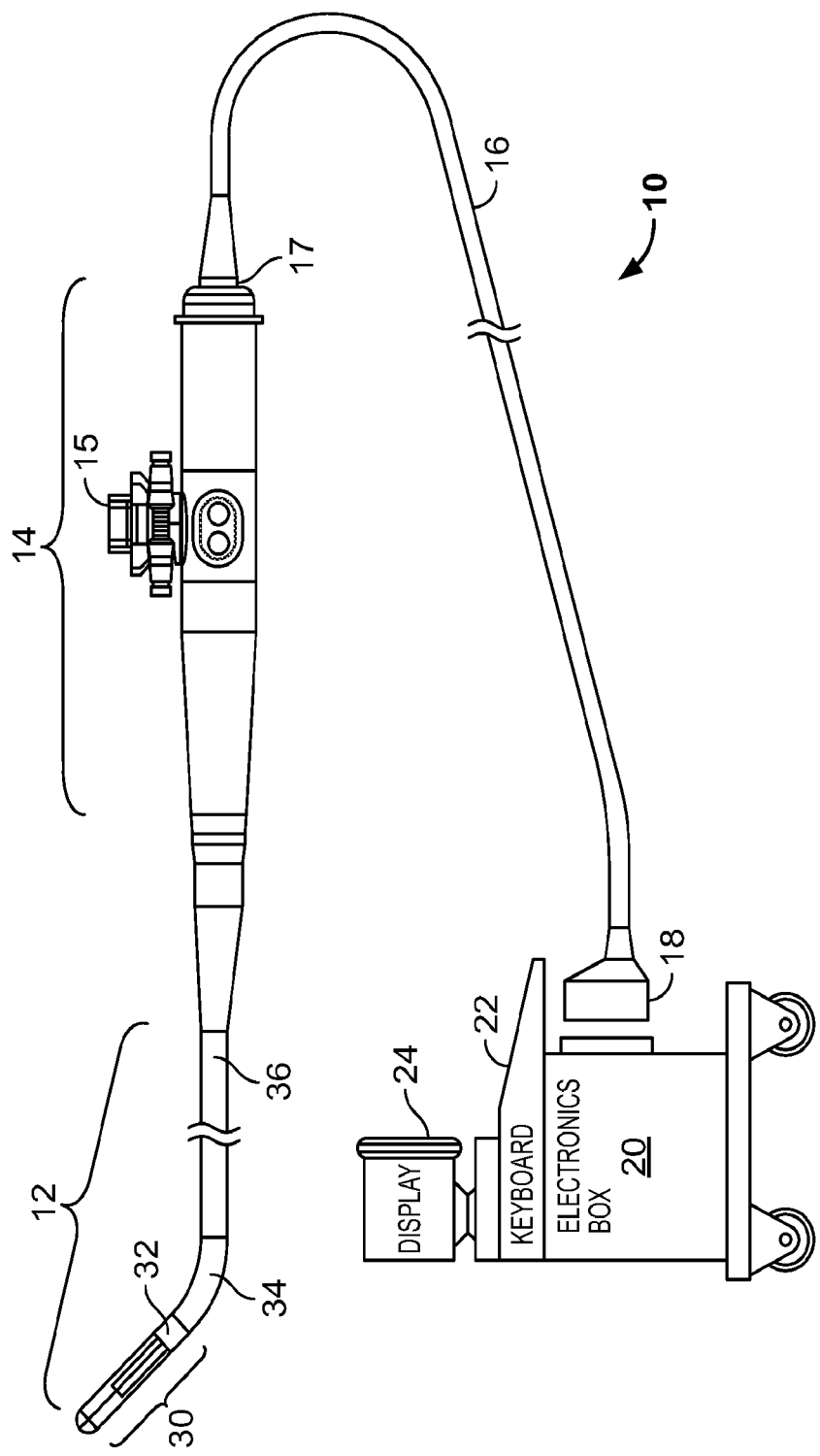
FIG. 1 illustrates an ultrasound system including a transesophageal imaging probe having a distal part and a semi-flexible elongated body.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Various endoesophageal balloon catheters, systems, and methods are described herein. A non-limiting exemplary application of the endoesophageal balloon catheters, systems and methods described herein is transesophageal echocardiography (TEE). In transesophageal echocardiography (TEE), an imaging probe is inserted through the mouth, and advanced into the esophagus. Ultrasound is transmitted from the probe tip, through the inflation medium of the balloon, for example, water, and to the adjacent target tissue.

Various TEE probes may be used in connection with the present invention. An example of one TEE probe is described in US Patent Publication 2011/0071395 to Miller et al. and assigned to Koninklijke Philips Electronics N.V., Eindhoven (NL). An example of a TEE probe is the sector array multiplane TEE and iE33 systems manufactured by Koninklijke Philips Electronics N.V., Eindhoven (NL).

With reference to FIG. 1, a transesophageal echocardiography (TEE) imaging system 10 includes a transesophageal probe 12 with a probe handle 14, connected by a cable 16, a strain relief 17, and a connector 18 to an electronics box 20. Electronics box 20 is interfaced with a keyboard 22 and provides imaging signals to a video display 24. Electronics box 20 includes a transmit beamformer, a receive beamformer, and an image generator. Transesophageal probe 12 has a distal part or head 30 connected to an elongated semi-flexible body 36. The proximal end of elongated part 36 is connected to the distal end of probe handle 14. Distal part 30 of probe 12 includes a rigid region 32 and a flexible region 34, which is connected to the distal end of elongated body 36. Probe handle 14 includes a positioning control 15 for articulating flexible region 34 and thus orienting rigid region 32 relative to tissue of interest. Elongated semi-flexible body 36 is constructed and arranged for insertion into the esophagus.

Transesophageal probe 12 can be made by using a commercially available gastroscope. The length and outer diameter may vary. For example, in embodiments the length ranges from 80-120 cm. And the outer diameter ranges from 15-30 French. The gastroscope is made, for example, by Welch Allyn (Skananteles Falls, N.Y.).

Figure 2:
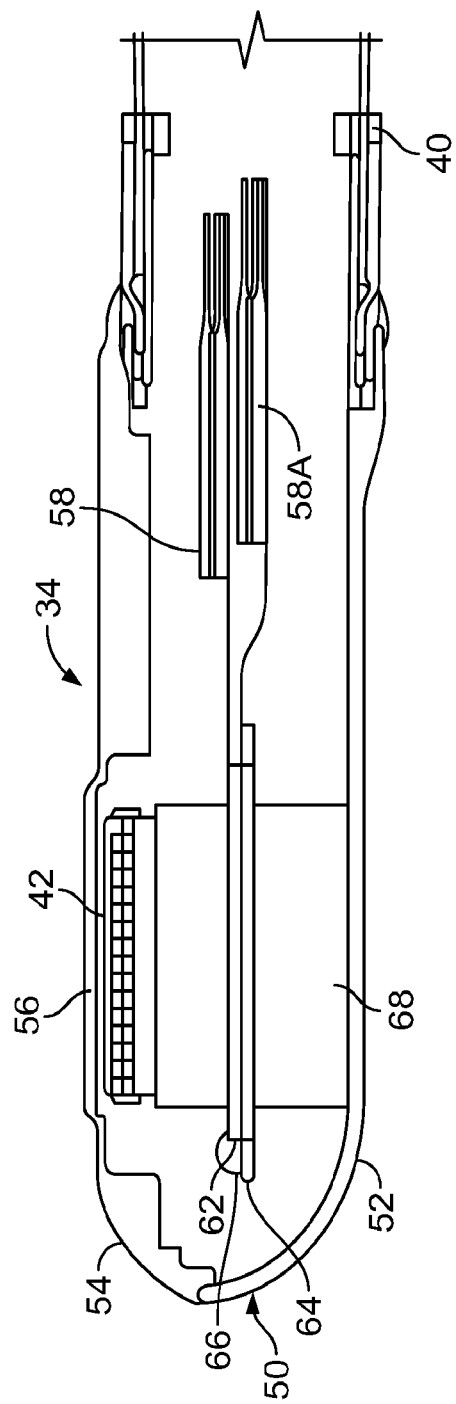
FIGS. 2 and 2A are schematic cross-sectional views of a rigid region of the transesophageal imaging probe shown in FIG. 1.
Figure 2A:
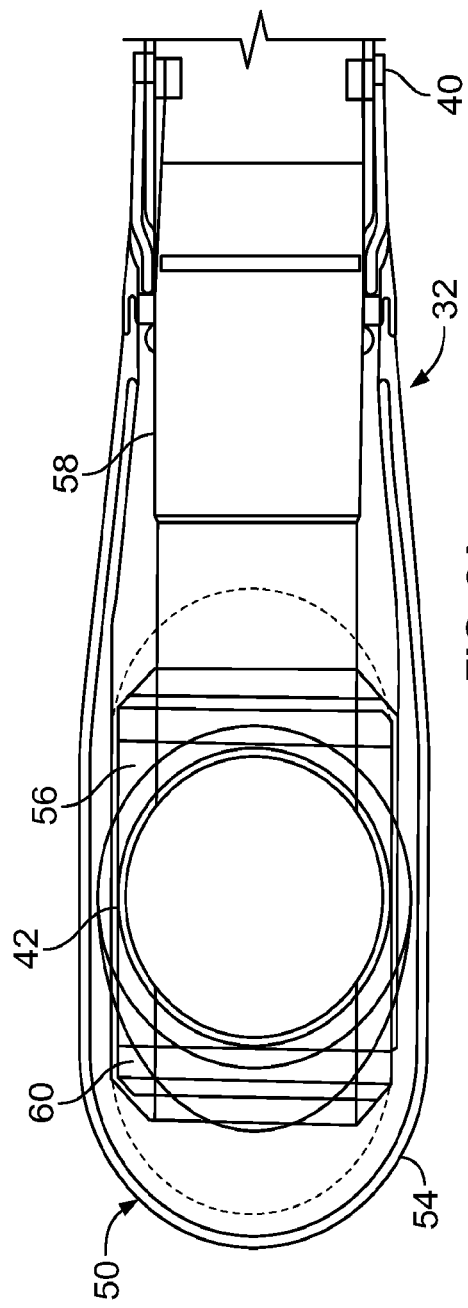

With reference to FIGS. 2 and 2A, the transesophageal imaging probe includes distal rigid region 32 coupled to flexible region 34 at a coupling region 40. Distal region 32 includes a distal tip housing 50 for encasing an ultrasound transducer array 42, electrical connections and associated electronic elements. Transducer array 42 is preferably a two-dimensional array of ultrasound transducer elements. Distal tip housing 50 includes a lower tip housing 52 and an upper tip housing 54 having a ultrasonic window 56 and a matching medium located in front of transducer array 42. The front part of tip housing 50 has a bullet shape with a rounded tip (or pill shape) for easy introduction into the fornix and advancement in the esophagus. Furthermore, housing 54 has a convex shape around window 56. Ultrasonic window 56 may also include an ultrasonic lens and a metal foil embedded in the lens material for cooling purposes.

Transducer array 42 is bonded to an array backing 60 and the individual transducer elements are connected to an integrated circuit 62, as described in U.S. Pat. No. 5,267,221. Integrated circuit 62 is connected to a circuit board 64 using wire bonds 66. This structure is thermally connected to a heat sink 68. The transesophageal probe includes two super flex circuits 58 and 58A, which provide connections between circuit board 64 and probe connector 18. The super flex circuits are arranged to have isotropic bending properties, for example, by folding into an accordion shape or by wrapping into a spiral shape. Alternatively, the super flex circuits may be replaced by a coaxial cable.

Figure 3:
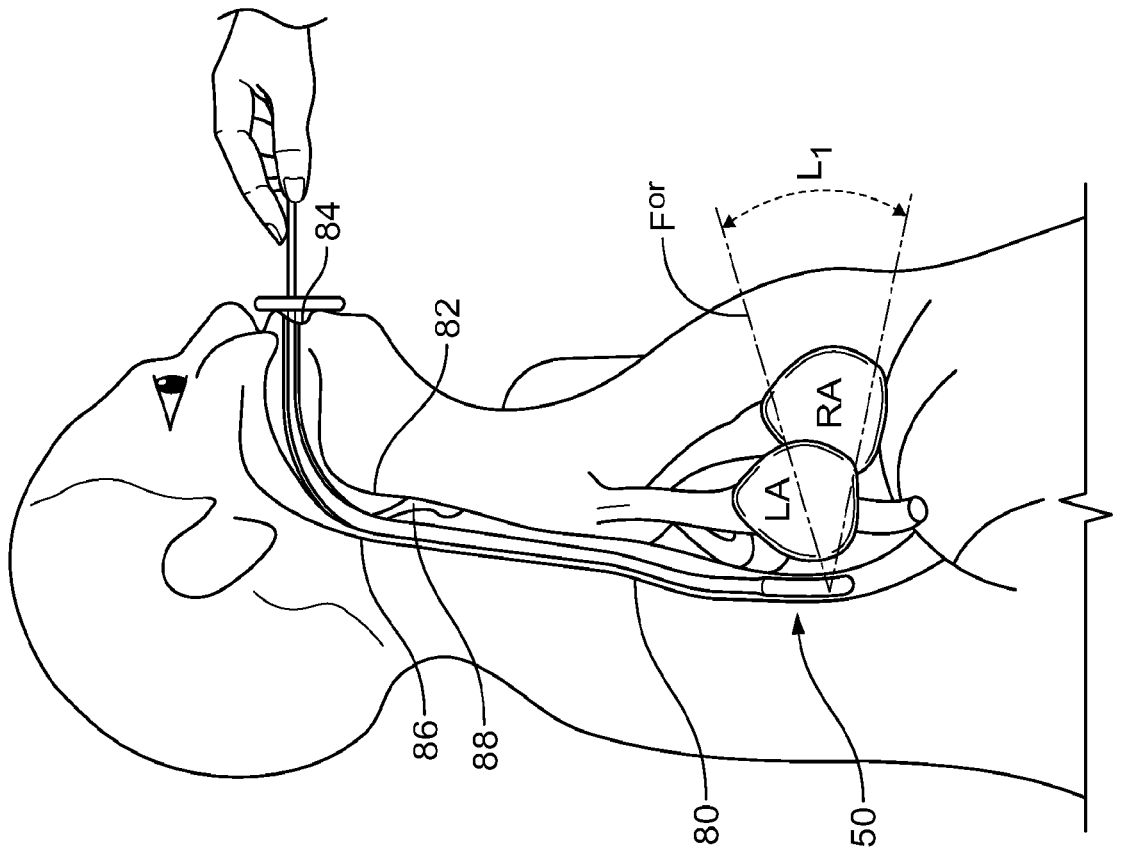
FIG. 3 illustrates introduction and use of the transesophageal probe for imaging of the heart.

With reference to FIG. 3, a clinician may introduce the transesophageal probe with an introducer 82 through the mouth 84, and into the esophagus 80. (alternatively, the TEE probe may be introduced through the nasal cavity.) After moving the probe and the introducer past epiglottis 88, distal head 50 of the probe is positioned inside the GI track at a desired location. Distal head 50 with transducer array may be positioned inside the esophagus 80. To image the heart, the ultrasound pulses are emitted from the array and the echoes from target structures are detected. Examples of target structures include the left and right atrium as well as tissue in the vicinity. However, as stated above, the FOV of current TEE probes is limited due to the contact pressure required with the esophageal wall to produce a satisfactory images.

Figure 4:
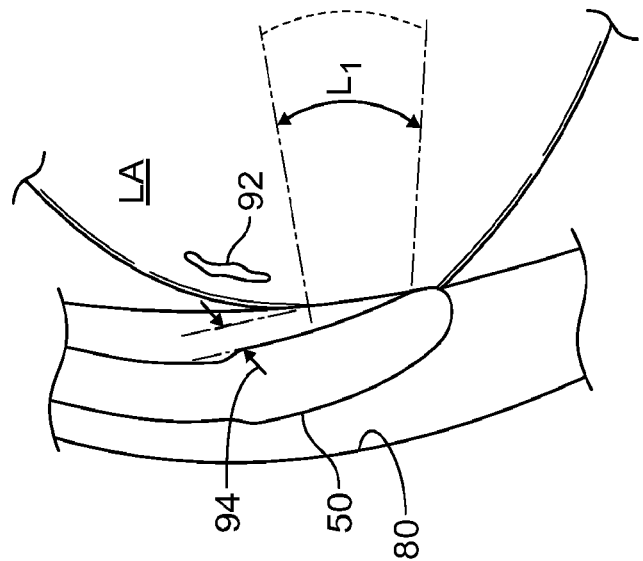
FIG. 4 is an enlarged view of a transesophageal probe in the esophagus.

FIG. 4 is an enlarged view of an imaging probe 50 in the esophagus 80. The left atrium (LA) is shown adjacent the esophagus. The array or head 50 is shown transmitting pulses through the esophagus towards structures of the left atrium. However, the pulse transmission is not optimal because an air gap 94 exists between the probe head and the esophagus wall. Additionally, the field L1 is limited because the probe head 50 is not optimally set back (namely, displaced) from the esophagus wall. There is not an adequate stand-off from the wall. Consequently, target structures (e.g., lesion 92) may be unclear, or worse, not visible using the probe head 50 under the circumstances shown in FIG. 4.

Additionally, although the probe head 50 may be manipulated or articulated, it is generally desirable to minimize the contact between the probe head and the abutting esophageal wall, yet limits severe scanning pressure, which may roughening or scarring the wall of the esophagus. Although scarring or tearing of the esophageal wall may not cause an imminent danger to the patient, bacteria and infection at the offended site may lead to the formation of a fistula, requiring surgical intervention. This is undoubtedly undesirable.

Figure 5C:
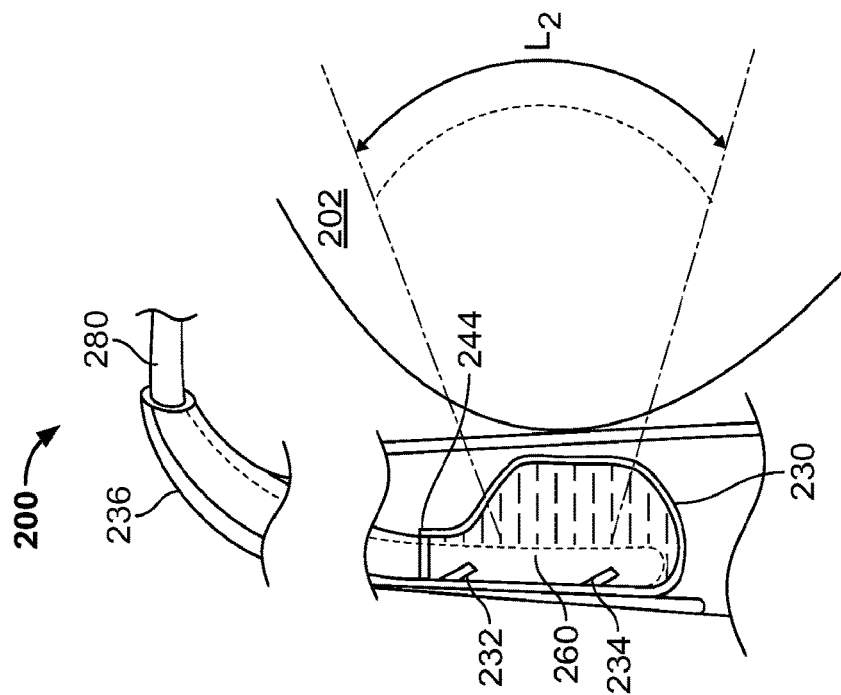
FIGS. 5A-5C illustrate advancing a transesophageal probe for imaging the heart in an endoesophageal balloon catheter.
Figure 5B:
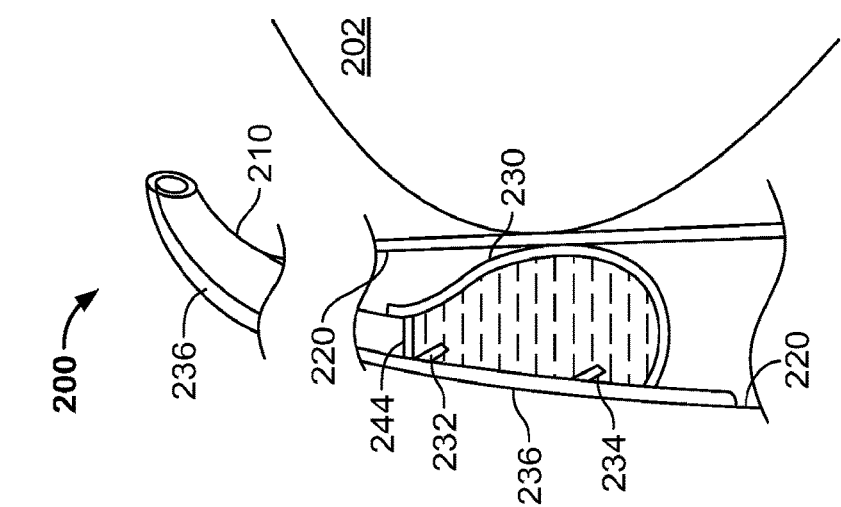
Figure 5A:
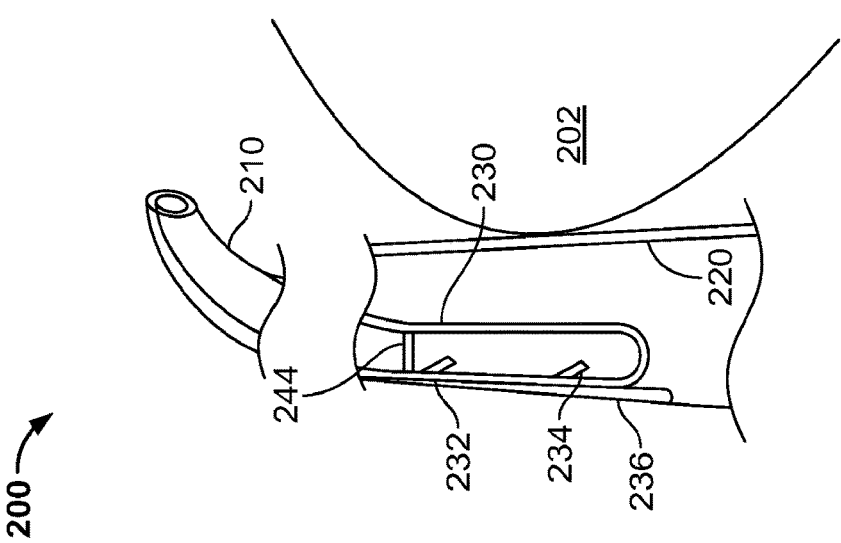

FIGS. 5A-5C illustrate a EEB catheter 200 in an application to image target structures (e.g., the left atrium 202 of the heart). Although the disclosure describes imaging the atrium, the invention is not intended to be so limited except where recited in the appended claims. The EEB catheter of this disclosure may be employed to image other structures, as well as adaptable to other endoluminal ultrasound situations such as endobronchial scanning.

With reference to FIG. 5A, the EEB catheter includes an elongate flexible shaft 210. Shaft 210 is shown extending in the esophagus 220. An inflatable member or balloon 230 is affixed to a distal section of the shaft. Non-limiting examples of material for the balloon include elastic rubbers and polymers. An example material is latex, or for patients with latex sensitivities, nitrile or isoprene rubber.

FIG. 5B illustrates the balloon 230 in an expanded or inflated state. The balloon is shown inflated with a liquid such as degassed water and/or saline. Inflation port 232 and deflation port to 234 are shown to respectively supply and/or remove liquid from the balloon. Valve, gasket or seal 244 prohibits the liquid from exiting the balloon. Seal 244 may be a slit valve, e.g., which can allow passage of the TEE there through as discussed herein, yet prohibit liquid from escaping the balloon. Water seal with the TEE shaft may also be accomplished by an external applied O-ring or inflatable ring prior to insertion of the TEE probe into the patient.

The balloon 230 is biased to expand in the direction of the ultrasound pulses emitted from the probe head or face. In embodiments, the front side of the balloon is free to expand whereas the backside is restricted in movement. To this end, in embodiments, a reinforcing member or stiffening member 236 is shown extending along the entire EEB catheter. The member 236 may be a wire, tube, or ribbon made of flexible or semi-flexible distal clip (described later) metal or polymer. The backside of the balloon may be bonded or held to stiffener 236 such that the balloon surface opposite the backside expands away from the stiffener. A thermal, mechanical, or adhesive bond may suffice to affix the stiffener to the balloon. Additionally, as will be described herein, the invention contemplates and includes alternative means to bias balloon expansion.

FIG. 5C illustrates a TEE probe head 260 advanced through seal 244, and into the EEB balloon member 230. Ultrasound energy from the TEE is sent through liquid within the balloon towards target atrium 202. The liquid or gel or medium is acoustically or ultrasonically conductive. Examples of suitable liquids include bacteriostatic and/or degassed water, or saline.

A field of view L2 is illustrated and captures a larger volume or area than field L1 shown in FIG. 4. Additionally, the transmission of the ultrasound waves is continuous through the liquid of the balloon and into the tissue. There are no are gaps or spaces between the esophageal wall and the transducer array. Additionally, the balloon creates a stand off from the heart tissue adjacent the esophageal wall, providing better visualization at this near zone region. Additionally, the balloon provides a smooth atraumatic cover surrounding the probe head, reducing the likelihood that the instrument may damage the tissue wall.

Figure 6B:
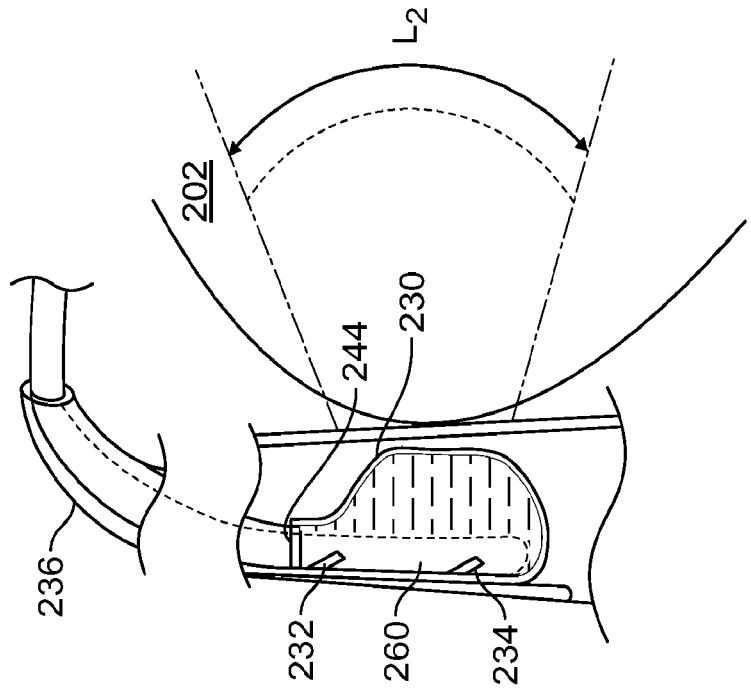
FIGS. 6A and 6B illustrate inflating the balloon of an endoesophageal balloon catheter in the esophagus.
Figure 6A:
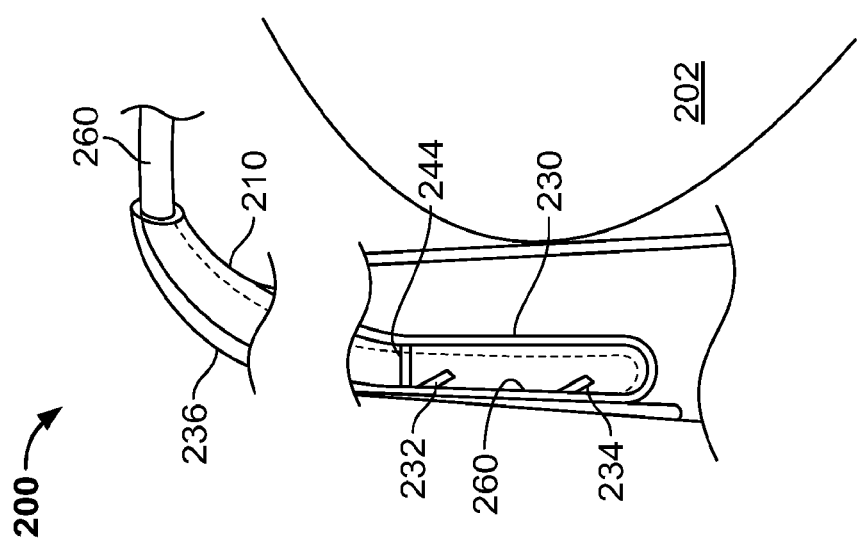

FIGS. 6A and 6B illustrate another embodiment of the invention. The embodiment shown in FIGS. 6A and 6B is similar to that shown in FIGS. 5A-5C except that TEE probe 260 is positioned in the EEB catheter 200 prior to inflation of the balloon member 230. A method includes inserting the EEB into the esophagus sans the TEE probe. The TEE probe is inserted into the EEB after the EEB is positioned as desired in the GI by the clinician.

FIG. 6B illustrates the balloon in an inflated state. The frontside of the balloon is setoff or displaced from the face of the probe head 260. Biasing the direction of the balloon expansion creates the advantages and applications described herein.

Figure 7A:
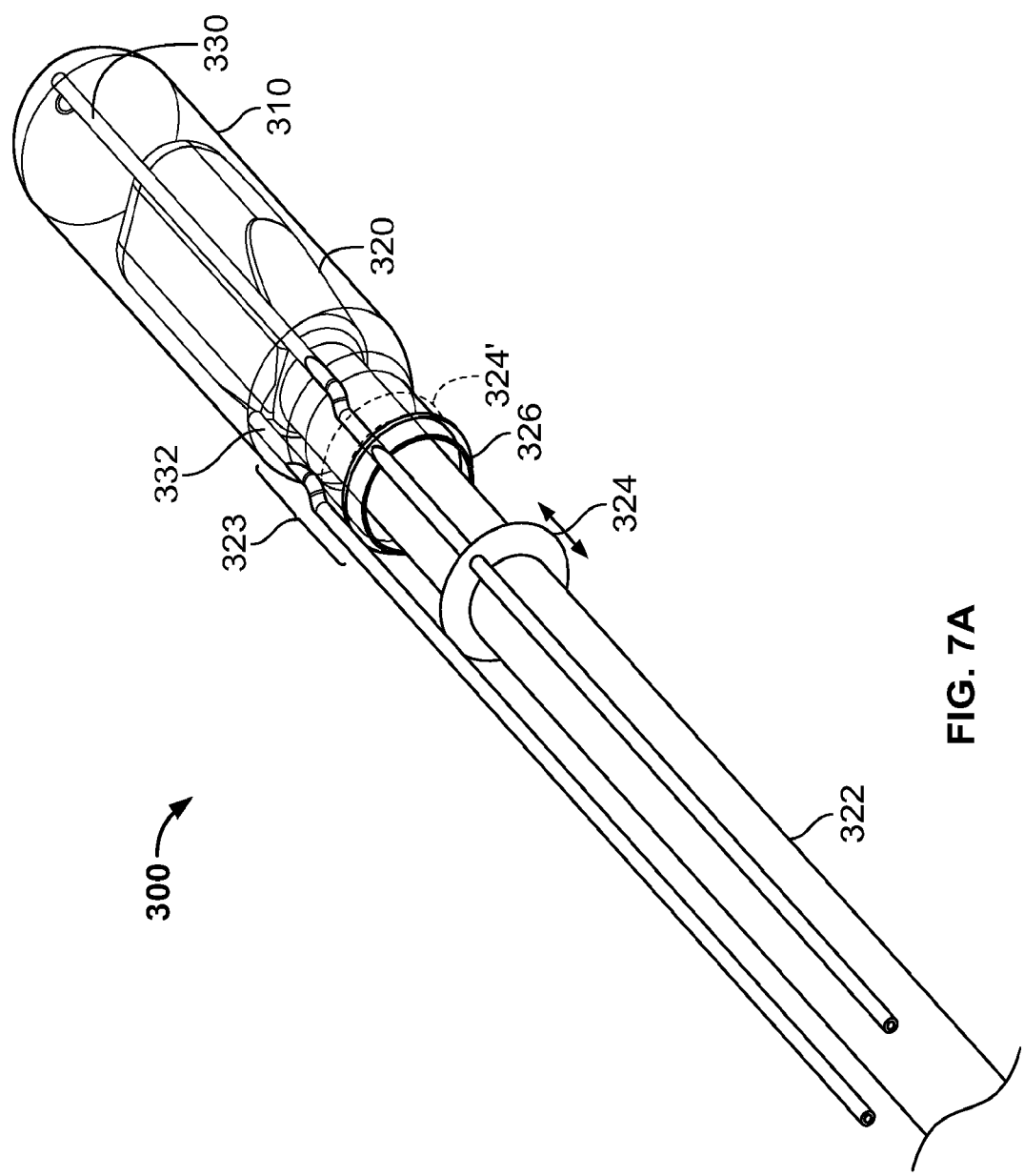
FIG. 7A is a perspective view of an endoesophageal balloon affixed to the distal section of a transesophageal probe for imaging.
Figure 7B:
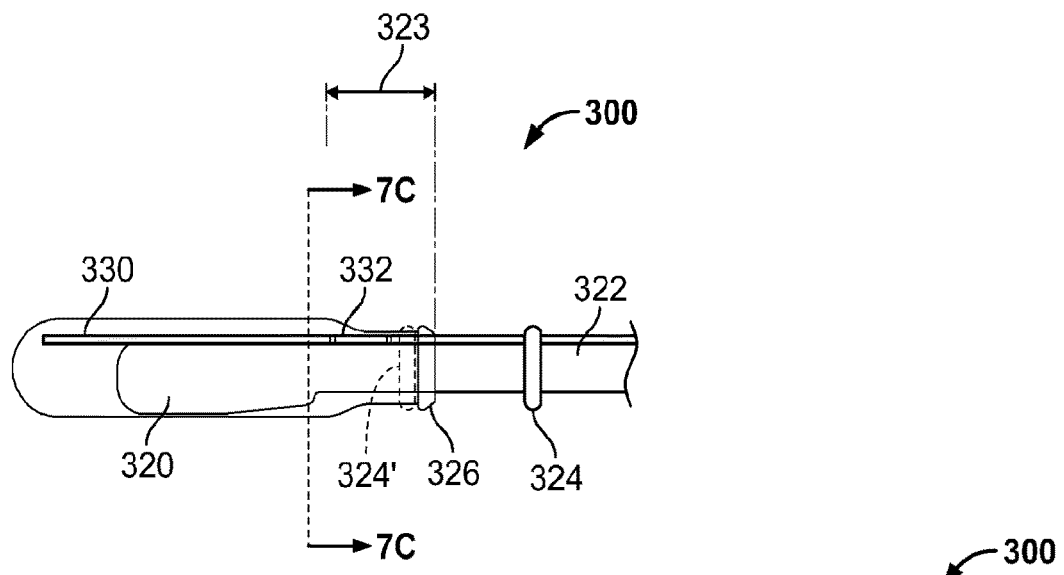
FIG. 7B is a side view of the endoesophageal balloon and transesophageal probe shown in FIG. 7A.
Figure 7C:
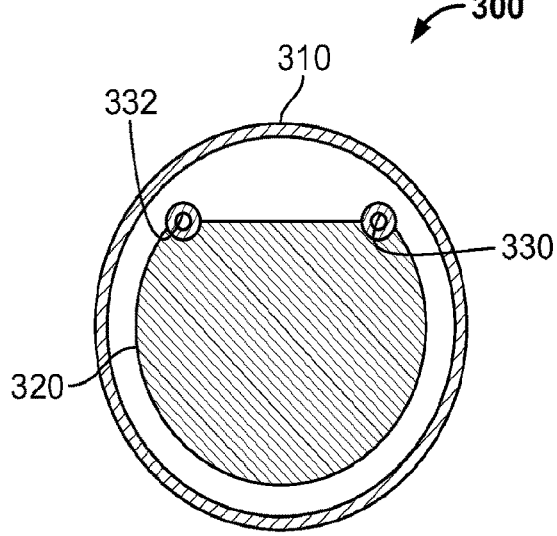
FIG. 7C is an enlarged cross sectional view of the endoesophageal balloon and transesophageal probe shown in FIG. 7B taken along line 7C-7C.

FIGS. 7A-7C illustrate an endoesophageal balloon assembly 300 comprising a balloon 310 surrounding the head 320 of a TEE probe. A proximal or neck region 323 of balloon 310 is shown loosely engaged to probe shaft 322. The balloon is preferably elastic so as to form a liquid tight seal on the shaft. However, the balloon portion covering the transducer window may fit more loosely to allow elastic expansion of the water imaging chamber surrounding the transducer head. Optionally, in embodiments, a sealing member 324 (for example an o-ring) may be manipulated to an assembled (or deployed) position 324' along the proximal region 323 of the balloon to bolster the integrity of the liquid tight seal. The proximal edge of the balloon may optionally feature an indent 326, barb, angle, interlock, or another structure to engage the sealing member or the shaft itself.

FIG. 7A also shows inflow tube 330 and outflow tube 332 to deliver and withdrawal liquid from the interior of the balloon 310 respectively. Tubes 332, 330 are shown extending proximally from the balloon towards the TEE probe handle (not shown).

Figure 8:
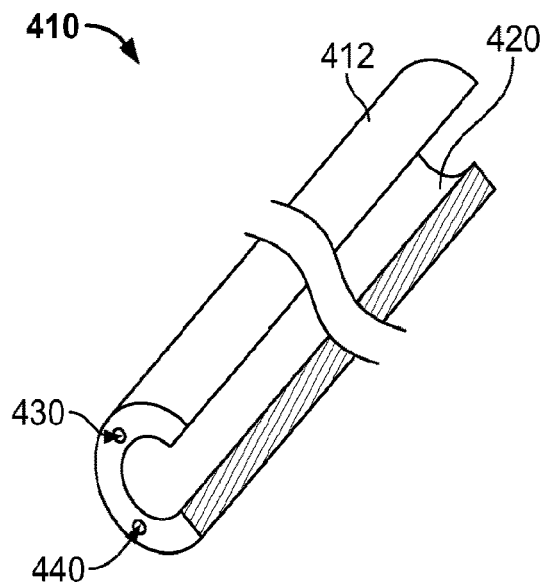
FIG. 8 is a partial perspective view of a endoesophageal balloon shaft. transesophageal probe for imaging

In other embodiments, for example as shown in FIG. 8, an elongate catheter member 410 includes a body 412 defining an open channel 420 adapted to lengthwise-engage the shaft 322 of the probe 320. Inflow and outflow liquid lumens 430, 440 are provided in the body 412 to supply and remove liquid to the balloon. A liquid tight connection is maintained as described herein. An example of a sealing feature includes an o-ring, gasket, and lip about the proximal neck region of the balloon to snugly accommodate the shaft of the probe. In embodiments the neck of the balloon may have a taper, decreasing in inner diameter in the proximal direction.

Figure 9A:
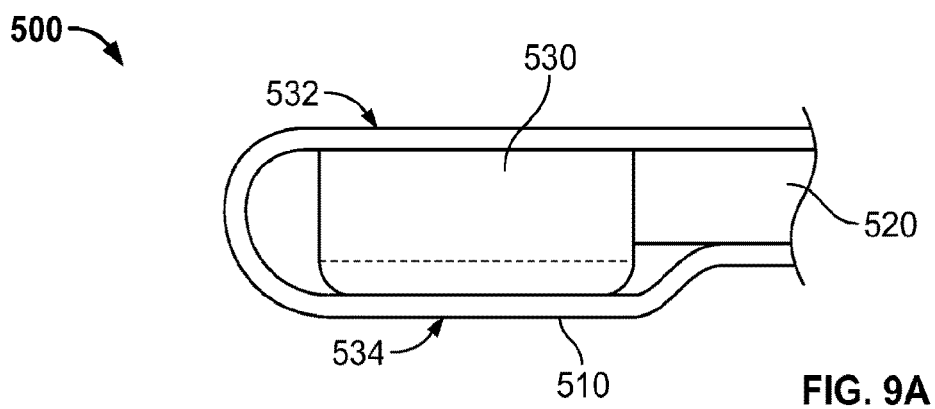
FIGS. 9A and 9B illustrate cross sectional views of another endoesophageal balloon affixed to the distal section of a transesophageal probe in an unexpanded and expanded state respectively.
Figure 9B:
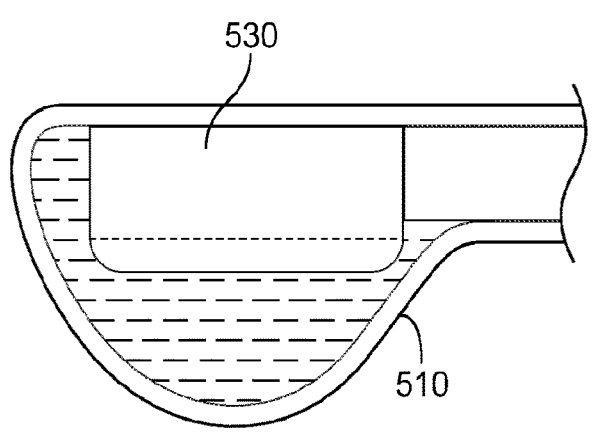

FIGS. 9A and 9B illustrate a partial side view of an EEB system including balloon member 510 surrounding image probe head 520. A clamp member 530 is shown affixed and covering the backside 532 and distal end of probe head, leaving the front side 534 and imaging window exposed. The balloon surface on the backside 532 is restricted, joined, or affixed to the clamp. Clamp 500 may be joined to the balloon via adhesives, heat, or mechanical bonds. The clamp may also be specially shaped and designed for each TEE head or manufacturer to allow a secure, yet flexible attachment and detachment.

The clamp is preferably detachably fixed to the backside of the probe head 520. Accordingly, when the balloon is inflated with liquid as shown in FIG. 9B, the balloon 510 expands directionally away from the transducer window. The balloon has biased expansion or preferential direction expansion. As described herein, amongst other things, expanding the balloon with bias direction creates a greater standoff from the target tissue, increasing the ultrasound field of view and improved near field visualization. The balloon is filled with an acoustically transmitting medium, enabling visualization of tissue structures that would not normally be visible under standard ultrasound technique because such structures would be too close to the transducer array.

Figure 10A:
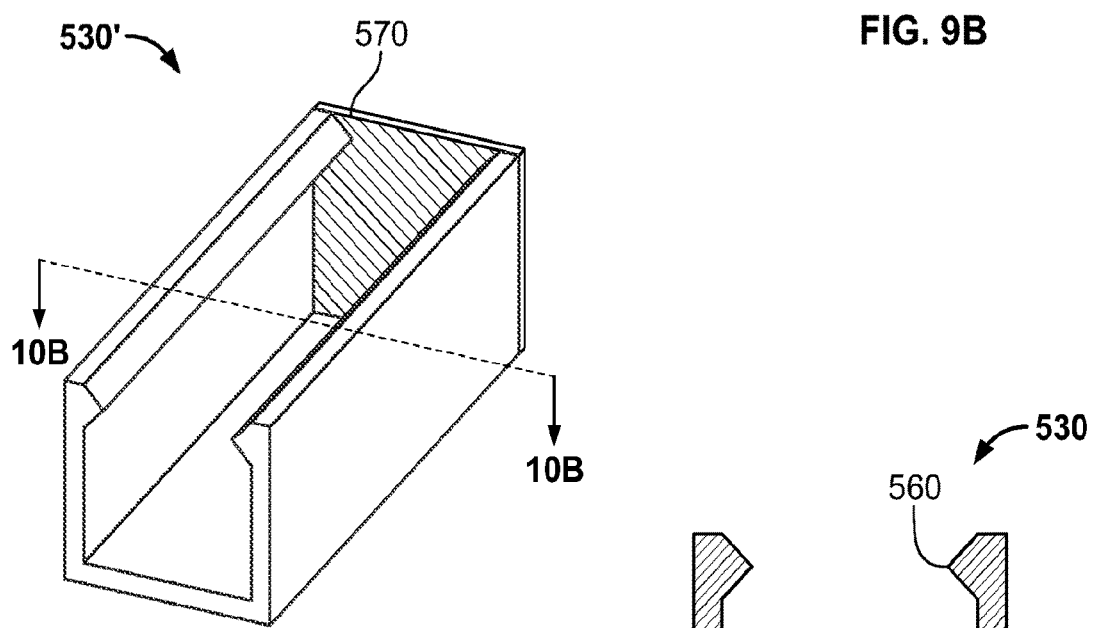
FIG. 10A illustrates a perspective view of a EBB clamp.
Figure 10B:
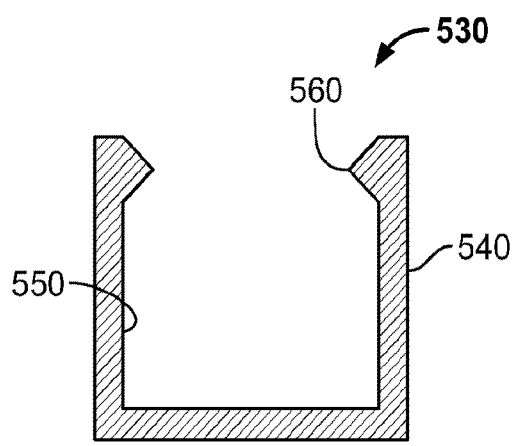
FIG. 10B illustrates a cross sectional view of the EBB clamp shown in FIG. 10A taken along line 10B-10B.

FIGS. 10 and 10B illustrate another clamp 530' to bias the balloon to expand directionally or asymmetrically. Clamp 530' includes a body 540 defining cavity 550 for receiving the probe head 520. Barbs 560 are disposed at the tips of legs of the body 540 for engaging with surfaces of the front side of probe head 520.

Additionally, clamp 530' is shown having a distal end wall 570 to restrict balloon expansion in the distal direction, that is, to restrict the balloon from expanding down the esophagus, and out of the intended imaging FOV.

There are various alternative means to limit the direction of the balloon expansion. In another embodiment of the invention, for example, the balloon comprises a variable thickness wall. The wall portion having the greater thickness (e.g., the backside portion) does not expand until the thinner lower pressure portion expands. A balloon thus may include a thin region to cover the transducer array window, and a thick region to cover the backside and end of the probe head. In embodiments, the thickness of the balloon along the restricted (backside and end) portion may be 2 to 10 times greater than that of the thin expandable (front side) portion.

The imaging probe can image target tissues as described above. Medical devices, such as a balloon catheter or an ablation catheter may also contain ultrasound visible markers. In this manner, an ablation catheter introduced into the left atrium of the heart may be displayed to the clinician. Position information of the instrument may be immediately observed and adjusted. Changes in the target tissue may also be observed in real time, and during treatment.

In still other embodiments of the present invention, a temperature regulated liquid may be circulated through the balloon. In a cryoablation procedure, for example, circulating a room or body temperature liquid through the balloon can act as a heat sink (or cold sink), serving to keep the esophageal wall at a viable (e.g., innocuous or non-lethal) temperature while ablation of nearby left atrial wall tissue is being performed, whether that be by cold temperatures of cryoablation, or hot temperatures from heat-generating sources such as radiofrequency, microwave, laser, etc.

For example, during a cryoablation procedure in the left atrium (LA), the cold may extend beyond the LA wall to the adjacent esophageal wall, and such cold would damage the esophageal wall but for the EEB described herein. In embodiments of the invention, a liquid or warm liquid is circulated through the EEB to warm the esophageal wall, thereby protecting the esophageal wall from freezing. The balloon inflation would be maintained at a constant pressure by regulating consistent flow of the fluid.

Examples of ablation procedures including endocardial cryoablation procedures and instruments for carrying out the same are described in PCT/US14/59684 to Yu et al., filed Oct. 8, 2014 and PCT/US2012/047487 to Cox et al., filed Jul. 19, 2012.

In embodiments, and in cases of RF or high temperature ablation, a cold or chilled liquid may be delivered through the balloon to mitigate heating of the esophageal wall. In embodiments, the pressure of the balloon is held constant. The pressure of the balloon may held constant by monitoring and maintaining the flowrate of the liquid through the balloon at a constant value.

Liquid delivery to the balloon may be performed using a handheld syringe as well as more sophisticated types of fluid delivery equipment including for example peristaltic pumps, while maintaining relatively constant and sufficient inflation pressure.

Figure 11:
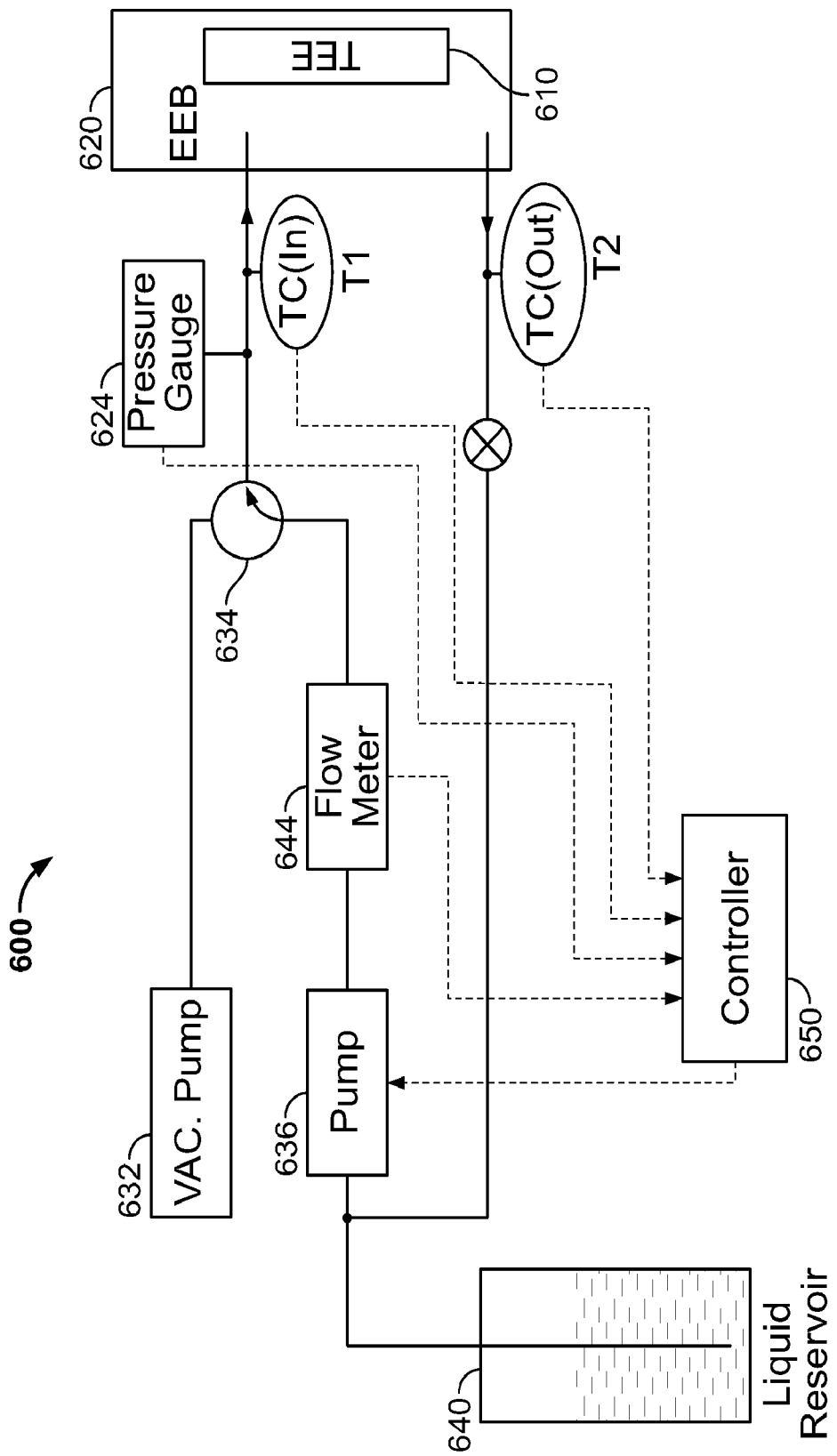
FIG. 11 illustrates an endoesophageal balloon and imaging probe system.

With reference to FIG. 11, a system 600 is shown including a TEE probe 610, and an EEB 620. EEB 620 is connected to a vacuum pump 632 via a three way valve 634.

Prior to commencing a procedure, the EEB 620 is evacuated to remove air bubbles. Additionally, in embodiments, the inner surface of the balloon may be treated with various coatings including a hydrophilic coating to facilitate removal of air bubbles and filling with the liquid.

A pump 636 is shown connected to valve 634. The valve is adjusted to allow liquid from the liquid reservoir 640, to be pumped to the balloon 620. A pressure gauge 624 and flow meter 644 are shown in line to the balloon to monitor pressure and flowrate respectively.

Pump 636 drives liquid at temperature T1 to the EBB 620. Controller 650 may be incorporated in the system to receive input and to control balloon pressure, and the liquid flowrate and/or other parameters of the system. For example, a controller may receive input including but not limited to the initial liquid temperature T1 and compare it to an exit temperature (T2) of the liquid exiting the EBB. The flowrate (as measured from flow meter 644) may be adjusted to maintain a predicted tissue temperature or removal of heat so as to preserve the esophagus or other healthy tissue, while maintaining sufficient pressure in the system to keep the balloon adequately distended and maintaining tissue contact with the esophageal wall. The flow circulation or heat sink supplied by the EBB thus serves to minimize collateral damage to tissue during an ablation treatment.

In an exemplary transesophageal application using the EEB catheter in combination with a TEE probe, ultrasound images are obtained of the internal heart chambers such as the left atrium, and in embodiments, the left atrium wall resolution may be more clearly observed. Sufficient contact and improved near FOV may facilitate overall visualization of other heart structures, such as all four pulmonary veins entering the left atrium.

In embodiments, the TEE probe includes a curved sensor array, and the EEB increases the field of view of the imaging array. Linear and curved transducer arrays cover a greater extent of tissue contact and the further expands the near field and overall FOV of the entire heart.

The imaging data arising from the ultrasound probe may be fused or overlaid with previously acquired 3D model data (e.g., CT data). This step may be performed in real time or near real time during a cryoablation procedure to observe and monitor the target location, progress of the left atrial wall ablation, and device position/location information.

Many modifications and variations of the present invention are possible in light of the above teachings. It is, therefore, to be understood that within the scope of the appended claims, the invention may be practiced otherwise than as specifically described.

What is claimed is:

1. An endoesophageal catheter for use with a transesophageal echocardiography (TEE) probe having an elongated body and, located at a distal section of the elongated body, a TEE probe head comprising a backside and a frontside in which ultrasound waves are emitted towards an anatomy to be visualized only from the frontside of the TEE probe head, the endoesophageal catheter comprising:
    an elongate shaft comprising a distal region, an open distal end, and a probe channel for slidably receiving said TEE probe; and
    an expandable member affixed to the distal region and enclosing the open distal end, the expandable member further comprising an open internal chamber adapted to slidably receive and enclose the TEE probe head when the TEE probe head is inserted into the expandable member such that a first wall portion of the expandable member directly covers the frontside of the TEE probe head and a second wall portion of the expandable member covers the backside of the TEE probe head, and to allow the TEE probe head to be slidable withdrawn from the expandable member, and
    wherein upon expansion of the expandable member, said first wall portion of the expandable member covering the frontside of the TEE probe head expands away from the TEE probe head a greater distance than the second wall portion of the expandable member covering the backside of the TEE probe head.

2. The endoesophageal catheter of claim 1, further comprising a reinforcing member, wherein the reinforcing member restricts expansion of the second wall portion of the expandable member.

3. The endoesophageal catheter of claim 2, wherein the reinforcing member is an elongate stiffener.

4. The endoesophageal catheter of claim 2, wherein the reinforcing member is a clamp affixed to the TEE probe.

5. The endoesophageal catheter of claim 1, wherein the expandable member is a balloon.

6. The endoesophageal catheter of claim 5, wherein the first wall portion has a first wall thickness and the second wall portion has a second wall thickness, wherein the second wall thickness is greater than the first wall thickness.

7. The endoesophageal catheter of claim 5, wherein the balloon further comprises a sealing member for receiving the TEE probe there through, the sealing member forming a fluid tight seal with the TEE probe and the balloon thereby preventing an inflation fluid from passing there through when the TEE probe is disposed within the balloon and the balloon is inflated with the inflation fluid.

8. The endoesophageal catheter of claim 2, wherein the second wall portion of the expandable member is held to the reinforcing member.

9. The endoesophageal catheter of claim 1, wherein the expandable member is expanded with an ultrasonically conductive inflation fluid, and wherein the inflation fluid is temperature regulated to maintain the esophageal wall at a viable (non-lethal) temperature during an adjacent cryoablation procedure.

10. The endoesophageal catheter of claim 7, wherein the elongate shaft further comprises a liquid inflow channel and a liquid outflow channel; and wherein the balloon is being inflatable upon delivery of the inflation fluid through the inflow channel and deflatable upon removal of the inflation fluid through outflow channel.

* * * * *